United States Patent [19]

Hogg et al.

[11] 4,189,236

[45] Feb. 19, 1980

[54] ELLIPSOID-CONIC RADIATION COLLECTOR AND METHOD

[75] Inventors: Walter R. Hogg, South Miami; Albert Brunsting, Miramar, both of Fla.

[73] Assignee: Coulter Electronics, Inc., Hialeah, Fla.

[21] Appl. No.: 888,560

[22] Filed: Mar. 20, 1978

[51] Int. Cl.² .......................... G01J 3/30; G01N 21/00
[52] U.S. Cl. .................................. 356/317; 250/461 B; 350/294; 356/39; 356/301; 356/336; 356/338
[58] Field of Search ................. 356/39, 301, 317, 318, 356/336, 337, 338, 339, 340, 341, 342; 250/222 PC, 461 B; 350/294

[56] References Cited

U.S. PATENT DOCUMENTS

| 1,278,026 | 9/1918 | Salto | 362/303 |
| 2,198,014 | 4/1940 | Ott | 350/294 |
| 3,494,693 | 2/1970 | Elmer | 353/55 |
| 3,946,239 | 3/1976 | Salzman et al. | 356/39 |

Primary Examiner—Vincent P. McGraw
Attorney, Agent, or Firm—William A. Newton

[57] ABSTRACT

Disclosed is a radiation collector apparatus and method primarily for counting and analyzing a flow of dilute particulate material, such as blood cells, sperm cells and the like, through the use of light detection. The radiation collector apparatus comprises a reflector chamber having an ellipsoidal reflector surface with a pair of elipsoidal foci defining a first focus, $f_{11}$, and second focus, $f_{12}$, and a second reflector surface with a primary focus, $f_{21}$, positioned at the same point as focus $f_{12}$, and a secondary focus, $f_{22}$. The second reflector surface has the configuration of one of the conic sections of revolution. In operation the radiation collector apparatus is provided with an intensifed beam of light and a stream of particulate material aligned to intersect the intensifed beam of light at focus $f_{11}$. Detectable light signals, after two reflections, are received in a focused beam by a photosensitive detector.

15 Claims, 13 Drawing Figures

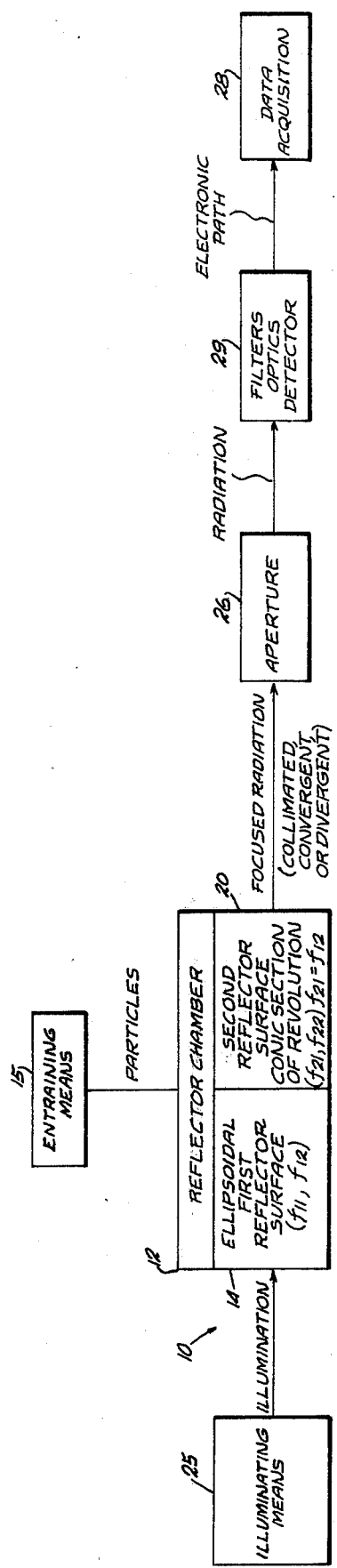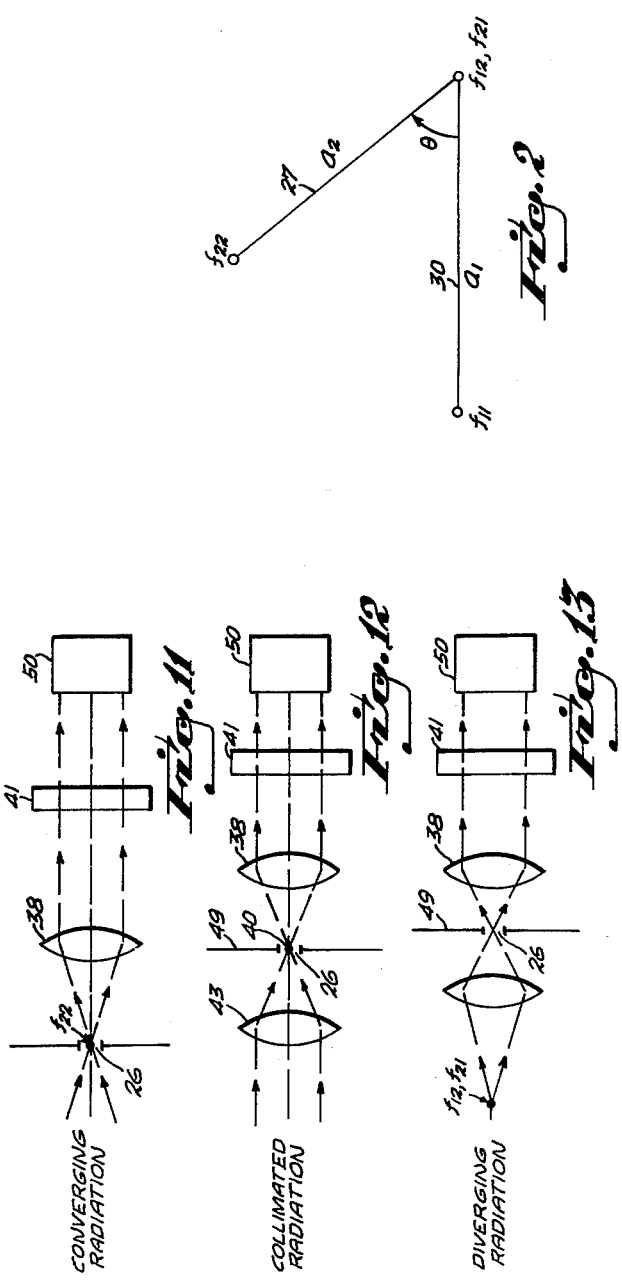

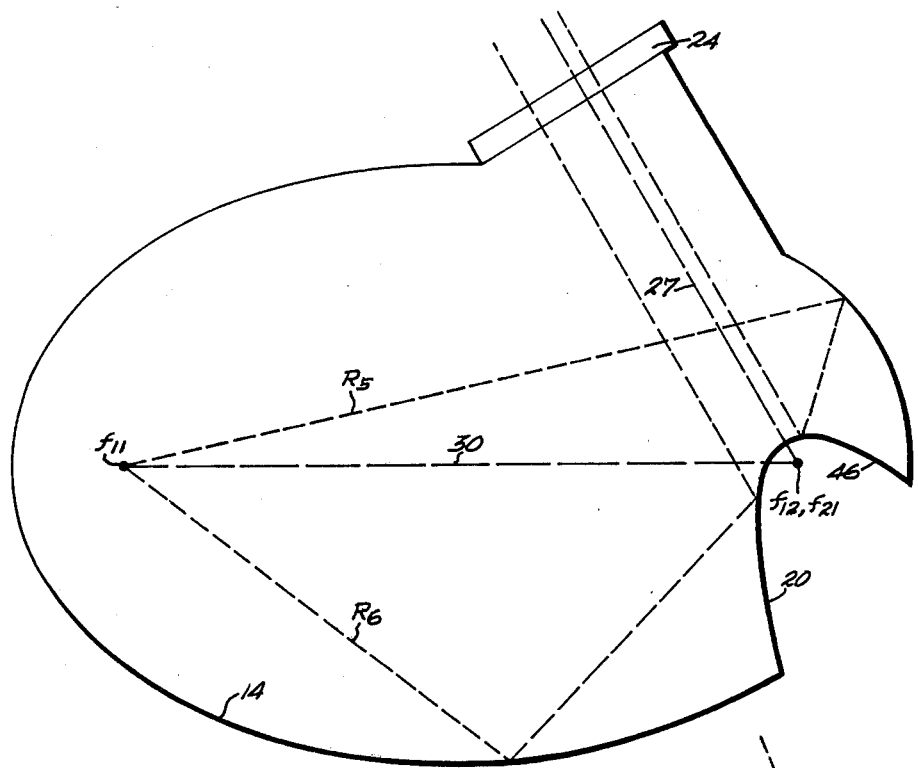
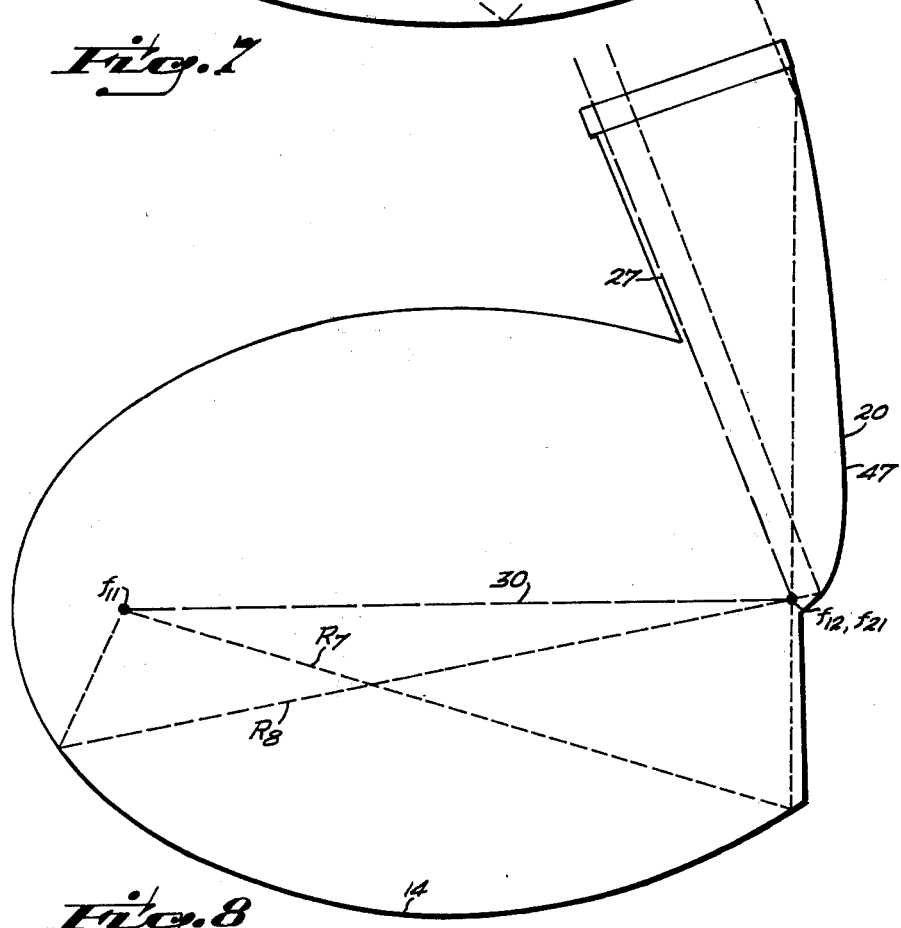

ELLIPSOID-CONIC RADIATION COLLECTOR AND METHOD

FIELD OF THE INVENTION

The present invention is directed to the collection of detectable light signals radiating from individually isolated particulate material, such detectable light signals being used for the counting and analysis of particulate materials.

DISCUSSION OF THE PRIOR ART

The quantitative measurement, counting and analysis of cells and like particulate material have become very important parts of biomedical research. Various flow cytometers exist in the prior art and have been devised to measure a range of cellular substances and properties, with some of these properties having to be measured on a cell by cell basis. The flow cytometers were improved by incorporating a laminar sheath-flow technique, which confines cells to the center of a flow stream, and a laser beam for intersecting the cell flow, which produces scattered light from the laser beam and/or fluorescent light from stained cells when the laser beam is at the proper wave lengths. Prior to U.S. Pat. No. 3,946,239, to Salzman et al, the cytometers were inefficient in collecting the scattered and fluorescent light, which made it difficult or impossible, in some cases, to investigate weakly fluorescing dyes bound to cells and fluorescence from small particles. More specifically, when there is inefficient collection of light, measurements of weak signals are made difficult due to the poor signal to noise ratio. The efficiency of light collection was improved by the ellipsoidal reflection chamber of U.S. Pat. No. 3,946,239. As disclosed in "The Journal of Histochemistry and Cytochemistry", Volume 25, No. 7, page 784, the flow chamber of U.S. Pat. No. 3,946,239 collects about sixty percent of the total cell fluorescence. Although this particular device made an improvement in efficiency of collecting scattered light and fluorescence, there are several inherent problems still remaining with the prior art as it has progressed up to and through U.S. Pat. No. 3,946,239, as will be discussed below.

First, in U.S. Pat. No. 3,946,239, most of the light that proceeds past the second focal point of the ellipsoidal flow chamber without any reflection off the ellipsoidal surface is lost for the purposes of collection. More specifically, the utilization of the end of the ellipsoid flow chamber for the placement of the conical reflectors decreases the total elliptical surface available for reflection and therefore decreases the collection angle and efficiency of the chamber. In addition, light reflecting off of the end of the ellipsoidal chamber converges at an extremely wide angle relationship relative to the center axis of the conical reflector, resulting in extremely inefficient use of the reflected light. Part of this inefficient use of light is due to multiple reflections of the light within the conical reflectors. The decrease in collection angle and efficiency in turn makes the chamber more sensitive to asymmetric particle orientation in the flow system, as well as lessening the ability to analyze weak fluorescent particles.

Secondly, in U.S. Pat. No. 3,946,239, when the light that is converged at the second focal point of the ellipsoid chamber is collected by the conical reflectors, the collected light is neither focused nor collimated and therefore arrives at the photosensitive measuring device in a disorganized manner at many different angles. The nonorthogonal approach of the collected light to the photosensitive measuring device reduces the efficiency of the photosensitive device and its filters in that such devices are best suited to light impinging orthogonally on their surfaces. Moreover, due to the light being disorganized, conventional means, such as lenses, for creating more orthogonal light cannot be used with the device of U.S. Pat. No. 3,946,237.

Thirdly, the orifice of the conical reflectors of U.S. Pat. No. 3,946,239, which collect the light is sufficiently large to allow stray light to be gathered. This orifice must be larger than the sensing zone (intersection of stream of particles and the laser beam). Additional width to the orifice is required by the wide angle convergence of the light at the second focal point and the extreme eccentricity of the ellipsoidal chamber. In U.S. Pat. No. 3,946,239 a pinhole orifice would be extremely inefficient, in that positioning would be critical in three dimensions and, if it were not perfectly positioned, practically no light would pass therethrough. This is due primarily to the light approaching the pinhole at angles widely different from the normal.

The cytometer of U.S. Pat. No. 3,946,239, although having a relatively good efficiency, can be described as being partially "blind". In other words, if light emanating from a particle is highly concentrated in some preferred solid half-angle, there is a possibility that it could be missed entirely even though this collector is efficient. More specifically, many particles are not spherical, but behave as combinations of oddly shaped mirrors and lenses, and hence cause "hot spots" in which large percentages of available light are directed in preferred directions. Consequently, in that this prior art cytometer does not collect light from all possible directions and collects light extremely inefficienctly in other directions, there exists the possibility of "hot spots" being aimed at a "blind" region. The net result is that some of the particles will cause some unpredictable percentage of the light emanating from them to be collected. This will smear a histogram generated by plotting the number of particles of a given intensity versus that intensity to the left, since many of the particles will appear dimmer than they actually are. Discrepancies of this magnitude are important. For instance, it is desirable to distinguish cells with X chromosomes from those with Y chromosomes, but at the present state of the art this is not possible.

It should also be noted that with the more efficient gathering of fluorescence and scattered light, the less powerful the laser beam needs to be, therefore leading to cost savings.

Other relevant prior art includes U.S. Pat. No. 3,494,693 to Elmer which teaches the use of coincident axis for reflecting means in the emission of heat. In addition, U.S. Pat. No. 3,989,381 discloses an inefficient light collector.

Accordingly, it can readily be seen that there is a need in the industry for a cytometer which is more efficient in collecting scattered light and fluorescence, and is more efficient in impinging the collected light on the photosensitive detectors. This increase in efficiency can result in being able to detect signals not previously detectable above the noise, decreasing the impact of the shape and orientation of particulate matter in the flow stream by eliminating "blind" regions, and allowing for lower powered lasers.

SUMMARY OF THE INVENTION

The present invention is directed toward a radiation collector apparatus and method for counting and analyzing particulate material, the apparatus comprising a reflector chamber including a first reflector surface in the form of an ellipsoidal reflector surface having a pair of ellipsoidal foci defining a first focus, $f_{11}$, and a second focus, $f_{12}$, and further including means for entraining the particulate material through the focus $f_{11}$. The reflector chamber further includes a second reflector surface having a primary focus, $f_{21}$, at focus $f_{12}$ and a secondary focus, $f_{22}$. The second reflector surface has a configuration of one of the conic sections of revolution. The apparatus is provided with detector means and a radiation restricting aperture intermediately positioned between the second reflector surface and the detector means on a symmetry axis defined by focus $f_{21}$ and focus $f_{22}$. The particulate material is illuminated with a radiation beam at focus $f_{11}$ to produce detectable radiation signals radiating outward, commonly in the form of fluorescent light and/or scattered light. After two reflections, the first on the ellipsoidal reflector surface and the second on the second reflector surface, radiation is converged in an organized beam toward focus $f_{22}$. Depending upon the embodiment of the second reflector surface, focus $f_{22}$ is positioned either at infinity and thereby causing collimation, or positioned in the vicinity of the detector means and thereby causing convergence, or is a virtual focus and thereby causing divergence. The focused beam emanating from the second reflector surface passes through the radiation restricting aperture to the detector means.

The method of collecting detectable radiation to analyse particulate material includes the steps of passing a stream of individual isolated particulate material through focus $f_{11}$ of the ellipsoidal reflector surface and illuminating the same with radiation to provide detectable signals in the form of radiation deviating from the path of the illuminating radiation. The method further includes the steps of reflecting radiation first from the ellipsoidal reflector surface and secondly from the second reflector surface so as to direct radiation in an organized beam to an area where the same will be processed. The method further includes the step of passing the organized beam proceeding from the second reflector surface through a radiation restricting aperture.

A primary object of the present invention is to provide a radiation collector apparatus and method having an increased collection angle of the reflector chamber, and therefore providing an increase in the total elliptical surface available for efficient radiation collection as compared to the current state of the art.

A related object of the present invention is to provide a radiation collector apparatus and method which incorporates a second reflector surface which leads to an increase in the available ellipsoidal reflector surface for efficient radiation collection.

Yet another related object of the present invention is to provide a radiation reflector apparatus and method having a greater total elliptical surface available for efficient radiation collection so as to be more sensitive to weak fluorescent signals and less sensitive to asymmetric particles, particle orientation absorption, refractive index, internal structure and surface properties of particles.

Another object of the present invention is to provide a radiation collector apparatus and method in which the detector means receives radiation substantially perpendicular to its photosensitive surfaces and its filters.

A related object of the present invention is to provide a radiation collector apparatus and method which incorporates a second reflector surface to converge a beam of organized radiation on focus $f_{22}$ whereby the photosensitive surfaces of the detector means do not receive radiation arriving at many different wide angles. The receipt of substantially normal radiation improves the efficiency of the detector means and its associated filters.

A related object of the present invention is to provide a radiation collector apparatus for converting a substantially $4\pi$ steradian solid angle ray distribution to a solid angle small enough to be collectable by an inexpensive lens.

Yet another object of the present invention is to provide a radiation collector apparatus and method having a radiation restricting aperture for filtering out stray radiation which does not originate in the focus $f_{11}$ from the particulate material.

Still another object of the present invention looks to the capability of using curves of smaller eccentricities while still maintaining high detecting efficiency.

Still another object of the present invention is to provide a radiation collector apparatus which redirects the radiation reflected off the ellipsoidal reflector surface towards a focus which can be optimally located with respect to the apparatus.

DESCRIPTION OF THE DRAWINGS

Further objects and advantages of the present invention will become apparent as the following description proceeds, taken in conjunction with the accompanying drawings in which:

FIG. 1 is a generalized diagrammatic representation of the preferred system according to the present invention.

FIG. 2 shows an exemplary graphical representation of the symmetry axis and foci of the radiation collector apparatus of the present invention.

FIG. 7 is a schematic cross sectional diagram of the convex paraboloidal reflector surface embodiment of the radiation collector apparatus.

FIG. 8 is a schematic cross sectional diagram of the concave paraboloidal reflector surface embodiment of the radiation collector apparatus.

FIG. 11 is a schematic representation of the lens layout for the embodiments having a convergent organized beam as in FIGS. 4 and 6.

FIG. 12 is a schematic diagram of the lens layout for the embodiment having a collimated organized beam as in FIGS. 7 and 8.

FIG. 13 is a schematic diagram of the lens layout for embodiments having a divergent organized beam.

DETAILED DESCRIPTION OF THE PREFERRED EMBODIMENTS

Figure 3:
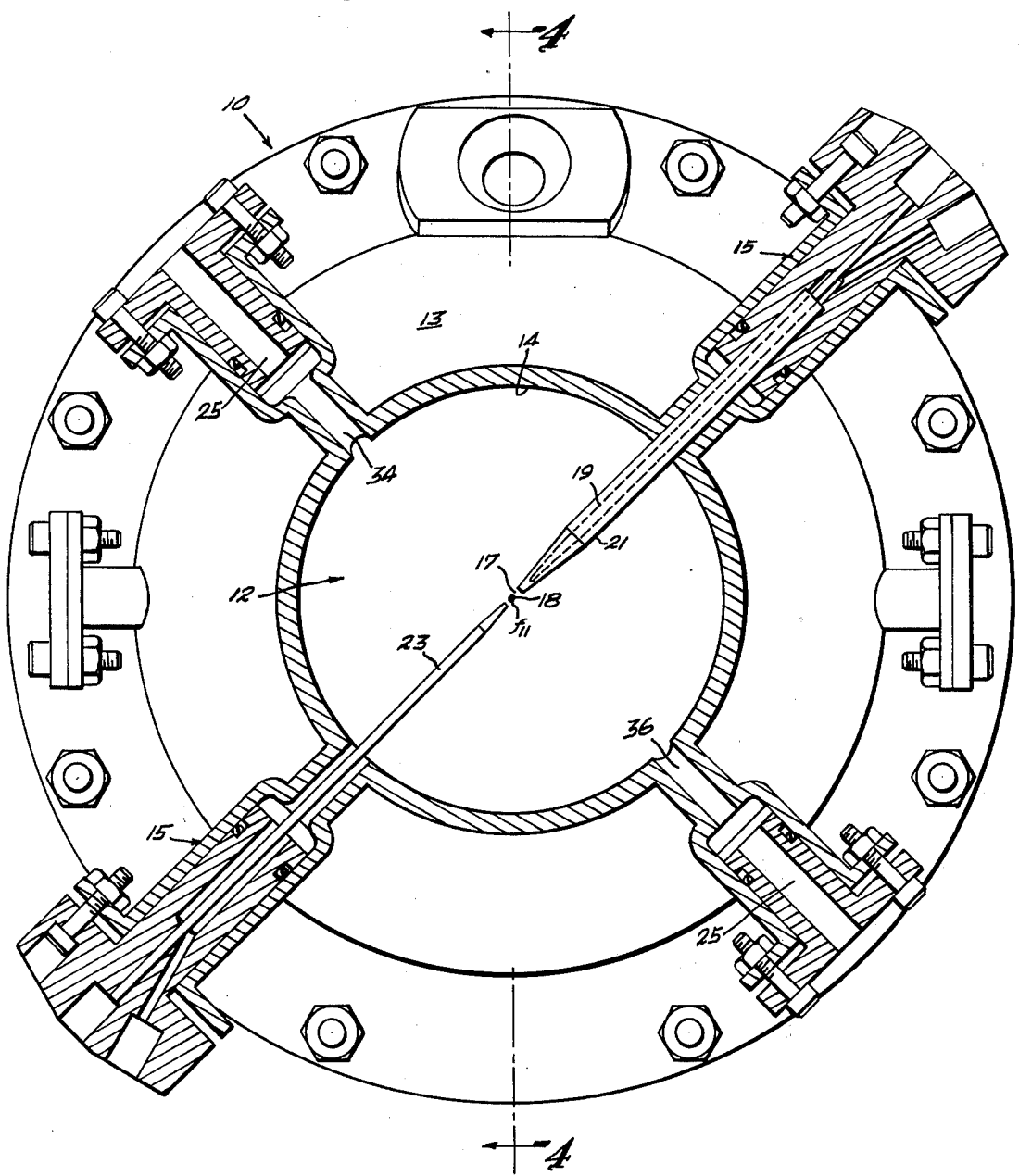
FIG. 3 shows a cross section of the radiation collector apparatus of the present invention taken along section line 3—3 of FIG. 4.

The radiation collector apparatus 10 is generally represented in structure and function in FIG. 1. More specifically, as shown in FIG. 3, the radiation collector apparatus comprises a reflector chamber 12 having a first reflector surface in the form of an internal ellipsoidal reflector surface 14 defined by a housing 13. The ellipsoidal reflector surface 14 has the configuration of an ellipsoid of revolution about the major axis, which is also known as a spheriod. As with all ellipsoids, ellipsoidal reflector surface 14 has first focus, $f_{11}$, and a second focus, $f_{12}$. By virtue of this geometry, light emanating from focus $f_{11}$ is reflected toward focus $f_{12}$ as illustrated by light rays $R_1$ and $R_2$ in FIG. 4. In the preferred embodiments the reflector chamber 12 is filled with a particulate-free liquid medium, although a chamber using a gaseous medium could be used with the present invention. Such an ellipsoid system, as described in this paragraph, is known to the art, as taught by U.S. Pat. No. 3,946,239.

Referring to FIG. 3, means for entraining the particulate material, generally indicated as 15, through focus $f_{11}$ of the ellipsoidal reflector surface 14 is in the form of fluid transport of the cells in suspension through a measurement region 17. More specifically, in the preferred embodiments an entrance tube 19 ideally provides a stream of sequential particulate material and outer sheath tube 21 encompasses the entrance tube 19 and provides sheathing fluid. Likewise, on the other end of the measurement region 17, there is normally positioned an exit tube 23 having an orifice for receiving the stream of particulate material. Laminar fluid flow is maintained through the measurement region 17 by the introduction of the sheathing fluid, along with the creation of a differential pressure between the quiescent volume and the sheathing fluid and the sample cell flow. The specific construction of the means for transporting the particulate matter through the measurement area 17 is of conventional design.

As depicted in FIG. 3, means for illuminating the particulate material with high intensity light, such as a laser beam, is generally indicated as 25. Illuminating means 25 comprises beam entrance orifice 34 and beam exit orifice 36. The two orifices 34 and 36 are aligned with each other so as to preferably, but not necessarily, intersect orthogonally the flow of cells in the measurement region 17, and to pass through focus $f_{11}$ of the ellipsoidal reflector surface 14. It should be appreciated that although laser light is used to illustrate the operation of the preferred embodiments of the present invention, the particulate material could be impinged upon by other forms of radiant energy as will become more apparent hereinafter.

In one type of analysis, the laser beam is scattered by the particles so that most of the scattered light will deviate from and not be received by the beam exit orifice 36. Another analysis commonly used in the industry is to excite fluorescence as the cells traverse the laser excitation beam. Fluorescent excitation is normally accomplished by staining the cells with a fluorescent dye and dispersing the cells into a suspension sufficiently dilute that they go one by one through focus $f_{11}$. In either case, there is typically scattered laser light and/or relatively weak fluorescent light. Consequently, the interaction of illuminating means 25 with the particulate material defines a radiation source 18 of detectable radiation at focus $f_{11}$. The above described procedure of having a laser beam intersect a sample stream of particulate material, possibly stained, at one of the foci of the ellipsoid is a well known procedure in the art.

Although scattered light and fluorescent light are commonly collected, it should be understood that the present invention may also be used to collect other forms of radiant energy from particulate material. Consequently, the term "detectable radiation" may include any radiant energy which propagates in straight lines and undergoes specular reflection, such as light, infrared radiation and ultraviolet radiation. However, for the purposes of describing the preferred embodiments, the term "light" will commonly be used.

In the practical application of the radiation collector apparatus 10, the foci $f_{11}$ and $f_{12}$ are actually focal zones and not theoretical points. The intersection of the particulate material, which may be the width of several particles, with the laser beam may create a "sensing zone" of radiating at focus $f_{11}$ having a volume of up to 10,000 cubic microns in the preferred embodiment. More specifically, the finite dimensions and somewhat diffused (Gaussian) distribution of radiation, convolved with the path of the particulate suspension, gives rise to this "sensing zone". This zone at focus $f_{11}$ is centered around a mathematical, infinitesimally small focal point and is represented in the drawings as a single point. As is well known in the art, a zone centered at the first focal point of the ellipsoid creates a corresponding zone of light centered at the second focal point of the ellipsoid. This principle is applicable not only for the first ellipsoidal reflector surface 14, but is also applicable for second reflector surface 20, to be described hereinafter. Although identified as a geometrical point for the purposes of illustration, the term "focus" as used in this disclosure refers to a focal zone consisting of all points from which light can progress in many directions and still pass through aperture 26.

As illustrated in the drawings, positioned at the end remote of the reflector chamber 12 relative to focus $f_{11}$ is a second reflector surface 20 comprising a conic section of revolution having a primary focus $f_{21}$, and a secondary focus, $f_{22}$. As depicted in FIG. 2, a straight line through foci $f_{11}$ and $f_{12}$ defines a first symmetry axis 30 for the ellipsoidal reflector surface 14. A straight line through foci $f_{21}$ and $f_{22}$ defines a second symmetry axis 27 for the second reflector surface 20. The first symmetry axis 30 is desirably disposed in angled relationship to the second symmetry axis 27 as represented by angle $\theta$. As shown in FIG. 2, $a_1$ represents the length between focus $f_{11}$ and $f_{12}$ and $a_2$ represents the length between focus $f_{21}$ and $f_{22}$. It will become apparent that $a_2$ may approach infinity in some of the embodiments described hereinafter. The second reflector surface 20 reflects light which is convergent on focus $f_{12}$ or $f_{21}$ toward focus $f_{22}$, with focus $f_{22}$ being optimally positioned.

Figure 4:
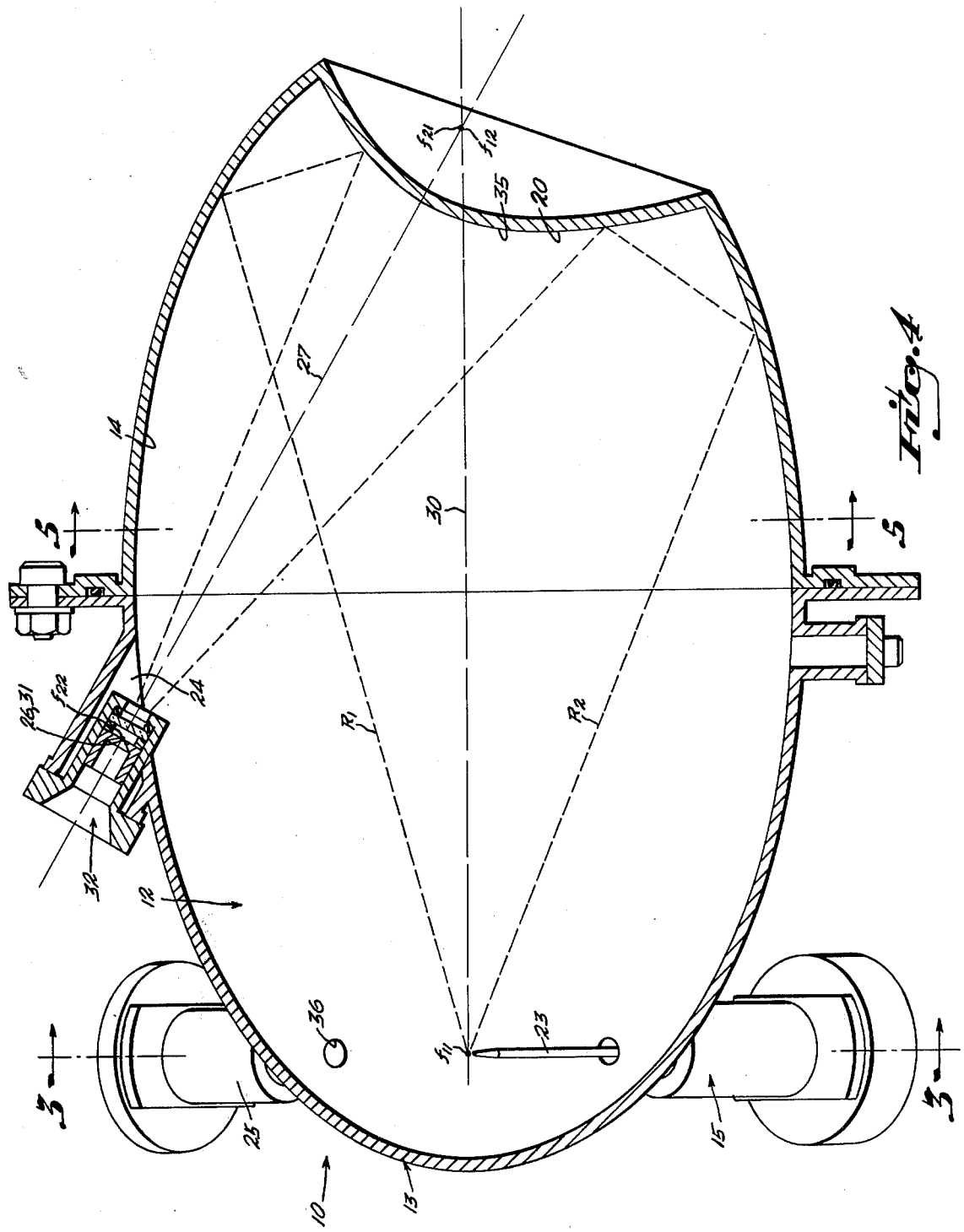
FIG. 4 shows a cross section of the radiation collector apparatus of the present invention taken along section line 4—4 of FIG. 3.
Figure 6:
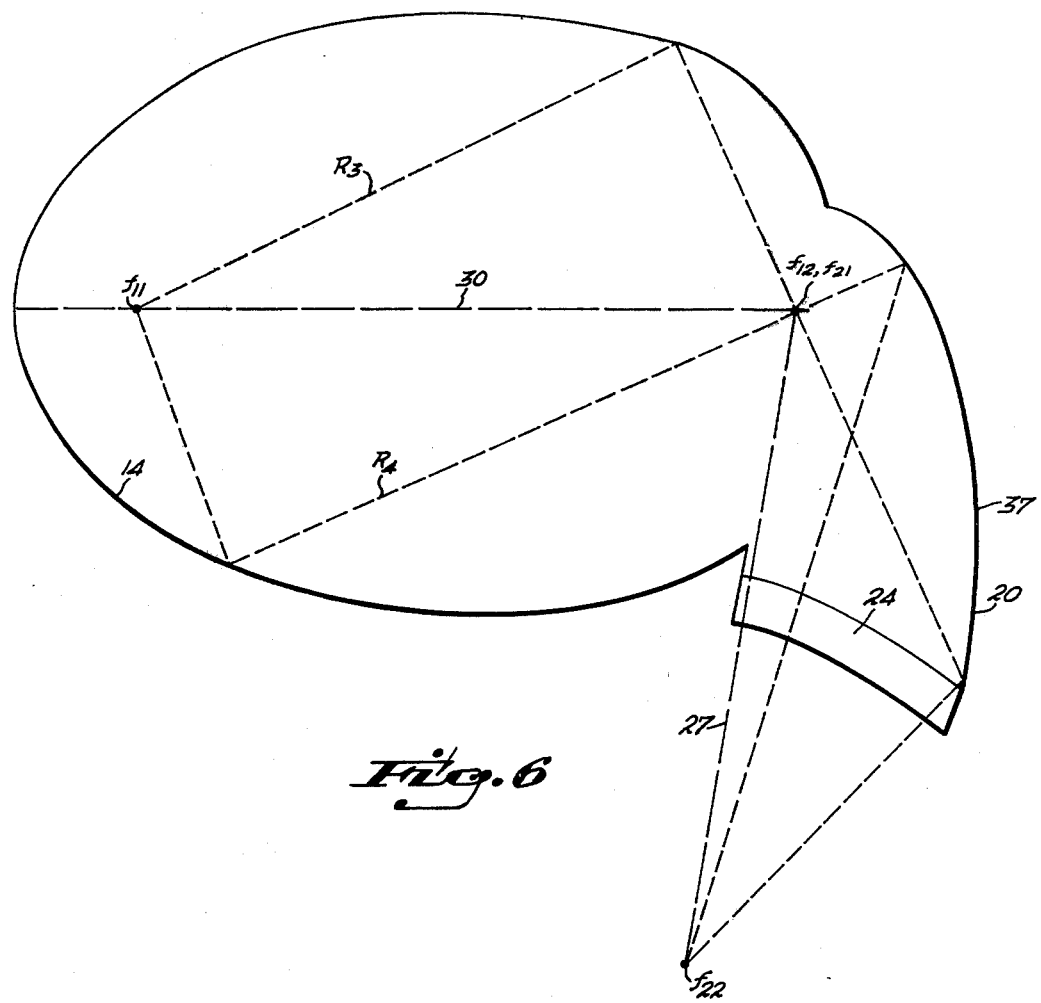
FIG. 6 is a schematic cross sectional diagram of the concave ellipsoidal reflector surface embodiment of the radiation collector apparatus.

There are several embodiments of the second reflector surface 20 which will be described hereinafter. All of these alternative embodiments of the second reflector surface 20 are conic sections of revolution having either a concave or convex relationship to the interior of the reflector chamber 12. Depending upon the embodiment, the focus $f_{22}$ is positioned near the periphery of the reflector chamber 12 or at infinity or is a virtual focus. When focus $f_{22}$ is positioned near the periphery of reflector chamber 12, the second reflector surface 20 may take the form of convex hyperboloidal reflector surface 35 or concave ellipsoidal reflector surface 37 as shown in FIGS. 4 and 6 respectively. When focus $f_{22}$ is positioned at infinity, the second reflector surface 20 may take the form of convex paraboloidal reflector surface 46 and concave paraboloidal reflector surface 47 as shown in FIGS. 7 and 8. When focus $f_{22}$ is a virtual focus, the second reflector surface means 20 may take the form of a concave hyperboloidal reflector surface (not shown). The above recited conic sections of revolution are not necessarily intended to be inclusive. To the contrary, it is intended that the scope of this invention encompass all second reflector surfaces 20 with a focus $f_{22}$, actual or virtual, positioned so as to allow collimated, convergent or divergent radiation directed along the symmetry axis 27 of the second reflector surface 20.

A distortion to the configuration of ellipsoidal reflector surface 14 can be introduced and compensated for by correspondingly modifying the second reflector surface 20 with the use of numerical techniques to provide for the focus $f_{22}$. Consequently, with the introduction of such distortions, both the ellipsoidal reflector surface 14 and the second reflector surface 20 would deviate from a precise conic section configuration but in combination would accomplish the same result. Also, the introduction of a relatively small distortion to the conic configuration of second reflector surface 20 produces a larger zone for focus $f_{22}$. Such a larger focus $f_{22}$ is not particularly desirable, but in certain applications is tolerable. It should be understood that such mere changes in configuration as described in this paragraph are considered to be within the scope of this invention, and for this reason the claims of this application use the term "substantially" when referring to the conic section configuration of the reflector surfaces.

A second reflector surface 20 having a focus $f_{22}$ at infinity will reflect light convergent on the focus $f_{12}$ or $f_{21}$ in a collimated organized beam along symmetry axis 27. A second reflector surface 20 having a focus $f_{22}$ near the periphery of the reflector chamber 12 will reflect light convergent on the focus $f_{12}$ or $f_{21}$ in a convergent organized beam along symmetry axis 27. A second reflector surface 20 having a focus $f_{22}$ that is a virtual focus as opposed to actual focus will reflect light convergent on focus $f_{12}$ or $f_{21}$ in a divergent organized beam. As is well known, a virtual focus for the focus $f_{22}$ would be disposed on the same side of the second reflector surface 20 as the focus $f_{21}$, thereby creating a divergent beam. Therefore the term "organized beam" is intended to be a generic description of divergent, collimated and convergent radiation proceeding along the symmetry axis 27 of the second reflector surface 20.

Figure 5:
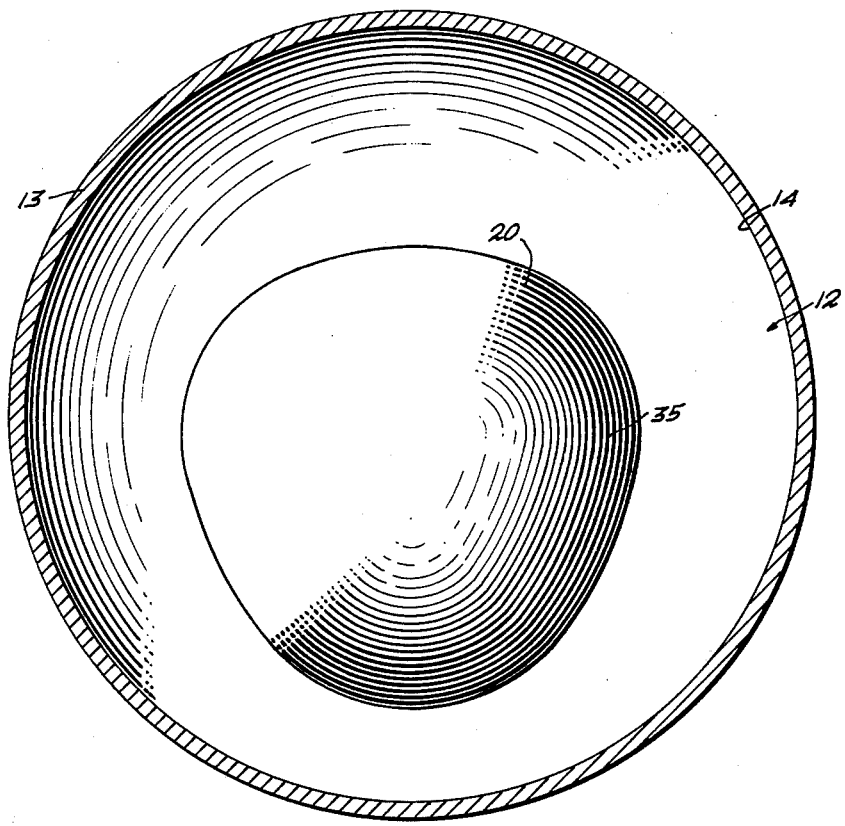
FIG. 5 shows a cross section of the radiation collector apparatus of the present invention taken along section line 5—5 of FIG. 4.

As depicted in FIGS. 4 and 5 the first and preferred embodiment of the second reflector surface 20 comprises the inwardly convex hyperboloidal reflector surface 35. A hyperbola is not a closed curve, but comprises two branches, with a focus interior to each branch. Referring to FIG. 4, it can be seen that the hyperboloidal reflector surface 35 is generated by the revolution of one hyperbola branch. With this embodiment, focus $f_{22}$ is preferably positioned in the vicinity of ellipsoidal reflector surface 14 enabling the use of the smallest possible aperture 26. Also, light converging on the focus $f_{12}$, $f_{21}$ is reflected prior to reaching the same in a convergent organized beam to focus $f_{22}$.

An alternative embodiment of second reflector surface 20 which is capable of providing a convergent organized beam is shown in FIG. 6. In this alternative embodiment, the reflector surface means 20 comprises the outwardly concave ellipsoidal reflector surface 37. Light passes through focus $f_{12}$, $f_{21}$ before being reflected by reflector surface 37 in a convergent organized beam, as illustrated by light rays $R_3$ and $R_4$ in FIG. 6. Ideally, in this embodiment exit window 24 comprises a spherical window for allowing the light coming from reflector surface 37 to exit from the reflector chamber 12. Such a spherical window would normally have outer and inner radii having a center at focus $f_{22}$ and would serve to retain the fluid in the reflector chamber 12. Such an exit window 24 allows the exiting light to pass orthogonally through its surfaces, minimizing intensity losses and refractive bending.

As illustrated in FIGS. 7 and 8, there are two alternative embodiments of the second reflector surface 20 which are directed toward having focus $f_{22}$ at infinity so as to provide a collimated organized beam from the same. As depicted in FIG. 7, the second reflector surface 20 comprises the inwardly convex paraboloidal reflector surface 46. As shown in FIG. 8, the second reflector surface 20 comprises the outwardly concave paraboloidal reflector surface 47. Exit window 24, in both of these embodiments, provides an exit for light proceeding from second reflector surface 20. Normally, exit window 24 comprises a flat window perpendicular to symmetry axis 27 and is used to retain the liquid in reflector chamber 12. The collimated organized light beam is illustrated in the one embodiment of FIG. 7 by light rays $R_5$ and $R_6$ and in the other embodiment of FIG. 8 by light rays $R_7$ and $R_8$. These collimating embodiments are a less efficient design because of large exit window 24 necessary for exiting light but may have advantage of economy (no further collimation needed) for some applications. Generally, if a converging lens 43, described hereinafter, is incorporated with the embodiments, the lens 43 and the reflector surface 46 or 47 are equivalent to the convex hyperboloidal reflector surface 35. More specifically as shown in FIG. 12, converging lens 43 takes focus $f_{22}$ from infinity and brings it nearby. Also, referring to FIG. 2, as $a_2$ of the convex hyperboloidal surface 35 approaches infinity, the same becomes convex paraboloidal reflector surface 46.

Yet another embodiment of the second reflector surface 20 (not shown in the drawings) results from replacing the concave paraboloidal reflector surface 47 of FIG. 8 with a concave hyperboloidal reflector surface. In such a second reflector embodiment, focus $f_{22}$ becomes a virtual focus, and the light proceeding from same forms a divergent organized beam. This type of divergent embodiment is less desirable in that a larger exit window 24 is required than for the other embodiments, but nonetheless supports the conclusion that the scope of the present invention includes a second reflector surface 20 capable of providing divergent light proceeding from the same. Furthermore, there are several other arrangements of conic sections of revolution which can direct light in a divergent organized beam, such as utilizing a portion downstream relative to the primary focus of a convex hyperboloid or concave or convex ellipsoid.

With all the above described embodiments for second reflector surface 20, the apparatus 10 preferably includes radiation restricting means 31. In the hyperboloidal reflector surface 35 embodiment, at the point where the symmetry axis 27 intersects the ellipsoidal reflector surface 14, there is ideally formed therein the radiation restricting means 31 in the form of a radiation restricting aperture 26 centrally located in exit window 24. Preferably the focus $f_{22}$ is centrally located within this aperture 26. As will become apparent during the discussion of the operation of the radiation collector apparatus 10, the aperture 26 is dimensioned and configured so as to narrowly circumscribe or encompass the organized beam of light proceeding from the second reflector surface 20 to the focus $f_{22}$. In this manner, the radiation restricting aperture 26 comprises basically a pinhole so as to filter out stray light, such stray light being light which does not originate at focus $f_{11}$. Stray light, in addition to that leaking into the reflector chamber 12 through the beam entrance orifice 34 and beam exit orifice 36, may be caused by imperfections or dirt on and fluorescence of the windows for orifices 34 and 36, or by scatter from irremovably small particles in the carrier fluid, and possibly by fluorescence of the carrier fluid itself. In the other three embodiments of the second reflector surface 20, radiation restricting means 31 may comprise a wall 49 disposed in spaced-apart relationship to exit window 24 and having the radiation restricting aperture 26 integrally formed therein as shown in FIGS. 11, 12 and 13. Additionally, in the two collimated organized beam embodiments of FIGS. 7 and 8, radiation restricting means 31 includes a converging lens 43 which has a near focus 40, as shown in FIG. 12. The inclusion of this lens 43 in these embodiments allows for the incorporation of a radiation restricting aperture 26 with pinhole dimensions. The hyperboloidal reflector surface 35 embodiment is particularly advantageous in that the aperture 26 can be formed in the exit window 24 of the reflector chamber 12.

Figure 9:
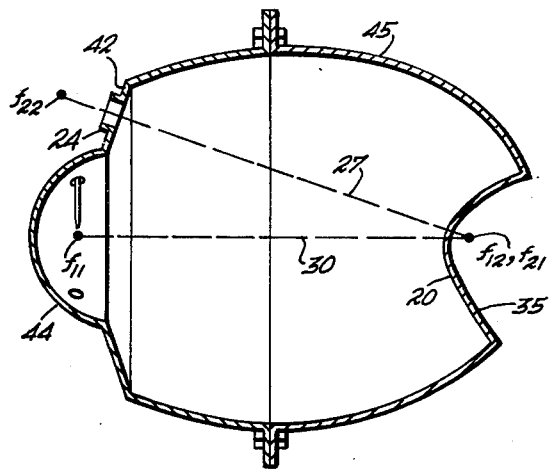
FIG. 9 is a schematic cross sectional diagram of a two confocal ellipsoids embodiment of the radiation collector apparatus.
Figure 10:
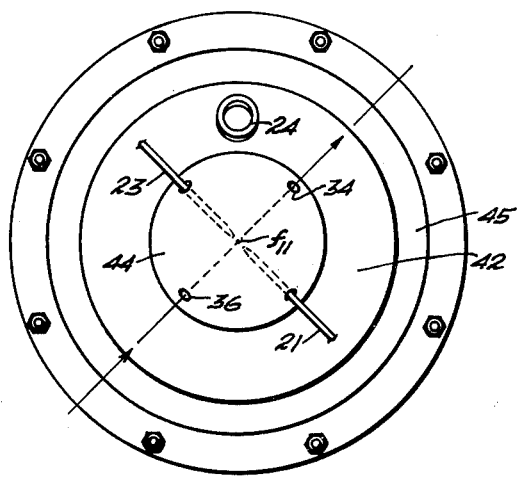
FIG. 10 is a schematic cross sectional diagram of the embodiment of FIG. 9.

Referring to FIGS. 9 and 10, there is shown an alternative modification to all four of the above-described embodiments, the two having focus $f_{22}$ at infinity and the two having focus $f_{22}$ adjacent the reflector chamber 12. This modification contemplates taking portions of two confocal ellipsoids and providing the ellipsoidal reflector surface 14 with a first ellipsoid portion 44 adjacent focus $f_{11}$ and an opposed second ellipsoid portion 45 constituting the remainder of the ellipsoidal reflector surface 14. The first ellipsoid portion 44 is defined by a segment of a first ellipsoid (not shown) having a pair of foci at focus $f_{11}$ and focus $f_{12}$. The second ellipsoid portion 46 is defined by a segment of a second ellipsoid (not shown) also having a pair of foci at focus $f_{11}$ and focus $f_{12}$. The first ellipsoid has a greater eccentricity than said second ellipsoid so as to provide a discontinuous area between the ellipsoid portions 45 and 44, thereby defining a gap 42. Gap 42 has exit window 24 formed therein to allow light rays to exit from the reflector chamber 12. More specifically, the symmetry axis 27 of reflector surface means 20 is disposed in intersecting relationship with the gap 42. The advantage of this embodiment is that the loss due to the solid angle of the exit window 24 is eliminated, as illustrated in FIG. 7.

In all of the embodiments heretofore described, detector means 29 is preferably positioned exterior to the reflector chamber 12 along the symmetry axis 27 for the conversion of detectable signals to electrical signals so as to provide subsequent data aquisition. Typically, but not necessarily, the detector means 29 is positioned outside the reflector chamber 12 in adjacent relationship to the aperture 26. The spacial relationships of detector means 29, aperture 26 and focus $f_{22}$ can be varied with the detector means 29 normally being located at or past the aperture 26 relative to the second reflector surface 20 along the symmetry axis 27. In FIG. 4, detector means 27 would be preferably positioned in cavity 32.

The specific construction of detector means 29 with its associated lens arrangements may be of many conventional designs well known to those skilled in the art. However, for the purposes of illustration, a typical detector means 29 for the convergent organized beam embodiments of FIG. 4 and FIG. 6 is shown in FIG. 11. Additionally, a typical detector means 29 for the collimated organized beam embodiments of FIG. 7 and FIG. 8 is shown in FIG. 12. Likewise, the detector means 29 for a divergent organized beam embodiment is shown in FIG. 13. The detector means 29 normally, although not necessarily, includes a light color filter 41, a collimating lens 38, and photosensitive detector 50, preferably in the form of photo multiplier tubes, vacuum photodiodes or solid state photo diodes and the like. Normally, although not necessarily, detector means 29 includes the collimating lens 38 for providing normal light to the photosensitive surfaces of the photosensitive detector 50. The more orthogonally that the focused beam arrives at the photosensitive surface of the photosensitive detector 50, the more efficient the photosensitive detector 50 will operate. Also, the optional light color filter 41 will also operate more efficiently with normal light. Generally, the narrow collection angle of the present invention permits the use of a less expensive lens 38.

As shown in FIG. 12 and FIG. 13 an additional converging lens 43 may be provided with the divergent and collimated organized beam embodiments so as to allow for the use of an aperture 26 having pinhole dimensions. Although use of these lenses 38 and 43 is preferred, they are not necessary for the operation of apparatus 10. For instance, by foregoing the use of a pinhole aperture 26 shown in FIG. 12, both lens 38 and 43 may be eliminated. Furthermore, by foregoing the pinhole aperture 26 in FIG. 13 and by foregoing having collimated light for the photosensitive surface of photosensitive detector 50, lenses 38 and 43 can be eliminated. Additionally, by foregoing having collimated light in FIG. 11, lens 38 may be eliminated.

As shown in the preferred design of the hyperboloidal reflector surface 35 embodiment of FIG. 4, the optimizing of the various design factors has led to the positioning of the exit window 24 in the mid-range portion of the reflector chamber 12 adjacent the minor axis of the same. In all the embodiments the positioning of the exit window 24, and therefore the detector means 29, is a compromise and other positions may prove desirable to those practicing the invention. More specifically, the direction of symmetry axis 27 and therefore angle $\theta$ of FIG. 2 is entirely unrestrained in the use of the radiation collector apparatus for particle analysis. An orientation is chosen which loses the least light at the juncture.

Referring to FIG. 1, in operation as a radiation collector, the radiation collector apparatus 10 preferably illuminates with a high intensity light beam the particulate material stream, commonly leading either to fluorescent light radiation or scattered light that proceeds outward in a radial manner from focus $f_{11}$. Except for the light which proceeds directly to the second reflector surface 20, the radiating light is reflected off of the ellipsoidal reflector surface 14, toward focus $f_{12}$, $f_{21}$. The light convergent toward focus $f_{12}$, $f_{21}$, undergoes a second reflection by the second reflector surface 20. This light, which was first reflected off the ellipsoidal reflector surface 14 and then off the second reflector surface 20, is now directed in an organized beam toward focus $f_{22}$. Depending on the embodiment, focus $f_{22}$ is ideally positioned either adjacent the reflector chamber 12 or at infinity. Generally, the light radiating outward to impact against the second reflector surface 20 is not reflected toward focus $f_{22}$, and is lost. The exception to this is the light which approximately passes directly between the two foci $f_{11}$ and $f_{12}$, $f_{21}$. The amount of this light will generally be dependent on the size of aperture 26. Light focused toward third focus $f_{22}$ passes through radiation restricting aperture 26, which filters out a substantial amount of the stray light. Thereafter, detector means 29 receives the light and converts the light into an electrical signal to be used in a conventional pulse height analyzer or similar well known data acquisition device 28.

As previously described, in particle analysis commonly either scattered light or fluorescent light will radiate outward from focus $f_{11}$ in distribution patterns known to those skilled in the art. As the light radiates outward from the focus $f_{11}$ it may take any radial direction in an imaginary sphere centered about focus $f_{11}$. The solid angle subtended will be utilized in this application to relate to the ellipsoidal surface area which is lost for reflection of light radiating from focus $f_{11}$. The collection angle therefore is the total possible angle of radiation $4\pi$ steradians, minus the solid angles of lost light collection. As examples of items that result in loss of collection angle, the following items are exemplary, but not exclusive. First, the outer sheath tube and exit tube 21 and 23 respectively, along with beam entrance and exit orifices 34 and 36 respectively, create four relatively small solid angles of loss. Additionally, the exit window 24, depending on the embodiment, may create an additional solid angle of loss. The largest solid angle of loss created is with the second reflector surface 20. The accumulation of all these solid angles described above results in the representation of ellipsoidal reflector surface 14 which is lost for the purposes of collecting light radiating from focus $f_{11}$. Consequently, the collection angle, representing the portion of the above-described imaginary sphere that will be available for light collection, will be decreased by all the above-described solid angles.

In the preferred embodiment of the hyperboloidal reflector surface 35, the formation of a larger collection angle relative to those existing in the prior art collectors creates a greater light collection efficiency. Moreover, in that the collected light is only reflected twice, the present invention is efficient relative to the prior art collectors. In addition, the radiation restricting aperture 26 eliminates and filters out stray light. Moreover, the relatively orthogonal approach of the rays to the detector means 29 and its light color filter 41 provides for efficient filtering and collection by the same. Additionally, the narrow collection angle of the detectable signals permits the use of a relatively inexpensive lens 38 if it is desirable to incorporate one into the detector means 29.

It should be noted that with the analysis of particulate material, the particles normally are sufficiently small so that light blockage is relatively insignificant and therefore the optical axis 27 and 30 may be coincident with $\theta = 0$.

Although particular embodiments of the invention have been shown and described in full here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

Method

There is disclosed a method of analyzing particulate material, such as blood cells, sperm cells, and the like, through the use of light detection. As illustrated in FIG. 1, the method comprises the steps of passing a stream of individually isolated particulate material through the first focus $f_{11}$ of the ellipsoidal reflector surface 14 of reflector chamber 12 and illuminating such particulate material at the first focus $f_{11}$ with light to provide detectable signals deviating from the path of the illuminating light. Subsequently, the method includes the further steps of reflecting the detectable signals twice, once from the ellipsoidal reflector surface 14 and secondly from a second surface 20, so that the light emanates from the second reflector surface 20 in an organized beam. Additionally, the method includes the step of passing the organized beam from the second reflector surface 20 through a radiation restricting aperture 26 to filter out stray light prior to processing the organized beam for data acquisition.

What is claimed is:

1. A radiation collector apparatus for analyzing individually isolated particulate material by illuminating the particulate material to produce a source of detectable radiation, comprising:

a reflector chamber including a first reflector surface and a second reflector surface, said first reflector surface having a substantially ellipsoidal configuration with a first focus and a second focus defining a first symmetry axis, said first reflector surface having said first focus disposed at the source of detectable radiation, said second reflector surface having a primary focus and a secondary focus defining a second symmetry axis, said second reflector surface having said primary focus disposed at said second focus of said first reflector surface, said first symmetry axis being disposed in angled relationship with respect to said second symmetry axis, whereby detectable radiation converged toward said second focus of said first reflector surface is reflected by said second reflector surface in an organized beam without significant stray light for further processing and analysis.

2. The radiation collector apparatus of claim 1,
   said second reflector surface having a substantially conic section of revolution configuration.

3. The radiation collector apparatus of claim 2,
   said second reflector surface having said secondary focus at infinity, whereby a collimated organized light beam proceeds from said second reflector surface.

4. The radiation collector apparatus of claim 3, said second reflector surface comprises a substantially convex paraboloidal reflector surface.

5. The radiation collector apparatus of claim 3, said second reflector surface comprises a substantially concave paraboloidal reflector surface.

6. The radiation collector apparatus of claim 2, said second reflector surface having said secondary focus positioned in the proximity of said reflector chamber, whereby a convergent organized light beam proceeds from said second reflector surface.

7. The radiation collector apparatus of claim 6, said second reflector surface comprises a substantially convex hyperboloidal reflector surface.

8. The radiation collector apparatus of claim 6, said second reflector surface comprises a substantially concave ellipsoidal reflector surface.

9. The radiation collector apparatus of claim 1, means for illuminating the particulate material with light at said first focus of said first reflector surface to produce light deviating from the path of the illuminating light.

10. The radiation collector apparatus of claim 9, said light deviating from the path of the illuminating light comprising scattered light.

11. The radiation collector apparatus of claim 9, said light deviating from the path of the illuminating light comprising fluorescent light.

12. The radiation collector apparatus of claim 2, said first reflector surface comprising a first ellipsoid portion adjacent said first focus and an opposed second ellipsoid portion constituting the remainder of said first reflector surface,
said radiation ellipsoid portion defined by a segment of a first ellipsoid, said first ellipsoid having a pair of foci at said first focus and said second focus,
said second ellipsoid portion defined by a segment of a second ellipsoid, said second ellipsoid having a pair of foci at said first focus and said second focus,
said first ellipsoid having greater eccentricity than said second ellipsoid.

13. The radiation collector apparatus of claim 12, said first ellipsoid portion and said second ellipsoid portion defining therebetween a discontinuous portion,
said second symmetry axis of said second reflector surface disposed in intersecting relationship with an exit window mounted in said discontinuous portion,
whereby the organized light beam from said second reflector surface may exit from said reflector chamber without a decrease in the solid angle of collection.

14. The radiation collector apparatus of claim 1, said first reflector surface comprising a pair of confocal ellipsoid portions, a first ellipsoid portion and a second ellipsoid portion,
said first ellipsoid portion being positioned adjacent said first focus and said second ellipsoid portion constituting the remainder of said first reflector surface,
said first ellipsoid having greater eccentricity than said second ellipsoid.

15. The radiation collector apparatus of claim 1, detector means positioned on said second symmetry axis to face said second reflector surface,
radiation restricting means having a radiation restricting aperture interposed between said second reflector surface and said detector means and aligned with said second symmetry axis, whereby said radiation restricting aperture filters out stray radiation.

* * * * *